(12) United States Patent
Mayer et al.

US011179179B2

(10) Patent No.: US 11,179,179 B2
(45) Date of Patent: Nov. 23, 2021

(54) IMPLANT FIXATION

(71) Applicant: SpineWelding AG, Schlieren (CH)

(72) Inventors: Jörg Mayer, Niederlenz (CH); Johan Van Havermaet, Deinze (BE)

(73) Assignee: SPINEWELDING AG, Schlieren (CH)

( * ) Notice: Subject to any disclaimer, the term of this patent is extended or adjusted under 35 U.S.C. 154(b) by 152 days.

(21) Appl. No.: 16/330,425

(22) PCT Filed: Sep. 7, 2017

(86) PCT No.: PCT/EP2017/072419
§ 371 (c)(1),
(2) Date: Mar. 5, 2019

(87) PCT Pub. No.: WO2018/046577
PCT Pub. Date: Mar. 15, 2018

(65) Prior Publication Data
US 2020/0222089 A1   Jul. 16, 2020

(30) Foreign Application Priority Data
Sep. 7, 2016 (CH) .................................. 01159/16

(51) Int. Cl.
*A61B 17/70* (2006.01)
*A61B 17/84* (2006.01)
(Continued)

(52) U.S. Cl.
CPC ........ *A61B 17/7059* (2013.01); *A61B 17/846* (2013.01); *A61B 17/8836* (2013.01);
(Continued)

(58) Field of Classification Search
CPC ..... A61B 17/70; A61B 17/7059; A61B 17/84; A61B 17/846; A61B 17/88; A61B 17/8836
See application file for complete search history.

(56) References Cited

U.S. PATENT DOCUMENTS

2007/0118243 A1* 5/2007 Schroeder .............. G16H 50/50
700/118
2010/0023057 A1* 1/2010 Aeschlimann ..... A61B 17/8047
606/246
(Continued)

FOREIGN PATENT DOCUMENTS

JP        2016-524506       8/2016
KR        10-0942170        2/2010
(Continued)

OTHER PUBLICATIONS

English translation of International Preliminary Report on Patentability dated Mar. 12, 2019 (Mar. 12, 2019), Application No. PCT/EP2017/072419, 6 pages.
(Continued)

*Primary Examiner* — Christopher J Beccia
(74) *Attorney, Agent, or Firm* — Rankin, Hill & Clark LLP

(57) ABSTRACT

An implant system that is designed to be fastened to a posterior side of a spinal column. The implant system includes an implant body, for example a plate, and a plurality of fasteners. The implant body has a fastening structure for each fastener. Each fastener extends between a proximal end and a distal end and includes a thermoplastic material in a solid state, the thermoplastic material being liquefiable by energy impinging on the fastener, in an anchoring process, in which the fastener is pressed against bone tissue by a pressing force acting from a proximal side, and in which energy is coupled into the fastener to at least partially liquefy the thermoplastic material, wherein a flow portion of the thermoplastic material is pressed into bone tissue and, after re-solidification, anchors the fastener in the bone tissue.

14 Claims, 9 Drawing Sheets

(51) Int. Cl.
*A61B 17/88* (2006.01)
*A61B 34/10* (2016.01)
*A61B 17/00* (2006.01)
*A61B 17/56* (2006.01)

(52) U.S. Cl.
CPC ............. *A61B 2017/00955* (2013.01); *A61B 2017/564* (2013.01); *A61B 2034/108* (2016.02)

(56) References Cited

U.S. PATENT DOCUMENTS

2015/0025585 A1* 1/2015 McCarthy ............... A61L 27/16
606/281
2018/0008349 A1* 1/2018 Gillman ................ A61F 2/4455

FOREIGN PATENT DOCUMENTS

| WO | 02/069817 | 9/2002 |
|---|---|---|
| WO | 2008/034276 | 3/2008 |
| WO | 2009/055952 | 5/2009 |
| WO | 2009/117837 | 10/2009 |
| WO | 2009/132472 | 11/2009 |
| WO | 2009/141252 | 11/2009 |
| WO | 2010/096942 | 9/2010 |
| WO | 2011/029208 | 3/2011 |
| WO | 2011/054122 | 5/2011 |
| WO | 2011/054124 | 5/2011 |
| WO | 2012/037700 | 3/2012 |
| WO | 2012/040863 | 4/2012 |
| WO | 2017/001851 | 1/2017 |

OTHER PUBLICATIONS

Switerland Search Report dated Jan. 13, 2017, U.S. Appl. No. 11/592,016, 6 pages.

* cited by examiner

IMPLANT FIXATION

BACKGROUND OF THE INVENTION

Field of the Invention

The invention is in the field of spinal implant systems.

Description of Related Art

Spinal implant systems include spinal implant fusion systems in which different vertebrae are fixated by a plate or rod relative to one another. Spinal implant systems may also include implants that fix a rib or the occiput or other bone tissue to the spine.

Of the spinal implant systems, posterior systems that include attaching the implant to a posterior side of the spinal column are preferred for many applications, as the posterior side tends to be much better accessible for the surgeon than for example the anterior side. However, the parts of the vertebrae that are accessible from the posterior side, namely the lamina, the spinous process and the transverse processes are relatively thin and therefore often not suited for a screw to be anchored therein. A possible solution are pedicle screws that extend through the pedicles into the vertebral body, but these are neither suited for all indications nor for all kinds of vertebrae. Therefore, often implants are fixed to the spinal column by an adhesive connection. Such connection, however, has well-known disadvantages especially resulting from the fact that the connection is only superficially, including only the outermost tissue layers. Therefore, in many situations the connection is not stable, and the patient has to undergo a further surgery.

SUMMARY OF THE INVENTION

It is therefore an object of the invention to provide an implant system, a method for its manufacture and a surgical method overcoming disadvantages of the prior art and being suitable for attachment to the lamina, the processes or tissue of adjacent thin, flat bone like a rib or the occiput.

According to an aspect of the invention, an implant system is provided, the implant system including:
  An implant body, for example a plate, the implant body having a shape being adapted to be fastened to the posterior side of the spinal column, and
  A plurality of fasteners,
  Wherein the implant body includes a fastening structure for each fastener,
  And wherein each fastener extends between a proximal end and a distal end and includes a thermoplastic material in a solid state, the thermoplastic material being liquefiable by energy impinging on the fastener, in an anchoring process, in which the fastener is placed relative to bone tissue, and in which energy is coupled into the fastener to at least partially liquefy the thermoplastic material, wherein a flow portion of the thermoplastic material is pressed into bone tissue and, after re-solidification, anchors the fastener in the bone tissue.

Especially, the fastener may be longer than a depth of the bone tissue. A length of the fasteners thus may be sufficient for the distal end face to reach through an opening in proximal cortical bone of the bone tissue and through cancellous bone of the bone tissue to be pressed against distal cortical bone of the bone tissue.

This especially pertains to the position of the fastener in the bone tissue of the patient's lamina, vertebral processes, ribs or occiput, as defined by the respective fastening structure.

This approach is based on the insight that, despite the limited depth, the bone tissue of lamina, processes, ribs or occiput is suited for the anchoring process that includes liquefying a thermoplastic material and letting it re-solidify after it has interpenetrated tissue. More in particular, it has been found that in an anchoring process in these bones, the distal cortical layer, which is not removed for the process, is suitable as counterface that offers mechanical resistance and friction if the fastener is pressed towards distally. Thereby, also comparably large amounts of thermoplastic material can be liquefied and displaced sideways into structures of the cancellous bone tissue, yielding a kind of foot of the fasteners for a rivet-like anchoring, and ensuring that the fastener has a large footprint, compared to an approach in which the distal end of a fastener is in the cancellous bone at the end of the process.

The anchoring process, as mentioned includes pressing the fastener towards distally, and coupling energy into the fastener. Thereby, thermoplastic material of the fastener becomes flowable at the distal end, and may be displaced by the pressing force acting on the fastener (and/or by other effects, for example adhesion). The process will also result in the fastener, or at least a thermoplastic portion thereof, being substantially shortened.

A design criterion may be that a length l along a proximodistal axis of a portion the bone level is greater, for example by at least a factor 1.5, than a cumulated thickness of the proximal cortical bone and of the cancellous bone. In this, the bone level is the level of the bone relative to the fastener after the anchoring process, and the length is the initial length referring to this level, i.e. the length before the process. After the process, due to the liquefaction, the axial extension below the bone level will generally be reduced.

In this, the mentioned thicknesses are generally defined because the fastening structure in most embodiments defines the position of the fastener with respect to the implant body and thereby, because the implant body is specifically shaped to be positioned relative to the posterior side of the spine, defines the position of the fastener.

The data necessary for estimating the bone thicknesses and also the length of the portion above the bone level may be obtained by 3D imaging methods. Such data, depending on the required precision and material properties, may also make possible that the implant body is custom manufactured.

As an alternative, the data, especially for standard cases, may be obtained based on well-known information on average sizes and properties.

In a group of embodiments, the fastener includes thermoplastic material (at least) at a distally facing end face, and the anchoring process includes pressing the fastener against bone tissue by a pressing force acting from the proximal side.

For example WO 02/069 817 and WO 2011/054 124 both describe methods of anchoring an implant in bone tissue, for example in spinal bone. However, the approaches described in these documents require a substantial depth of the bone tissue in which anchoring takes place, and they therefore demand, for spinal applications, that the liquefiable material is pressed into bone of the vertebral body, which has this depth. The present invention, in contrast thereto, combines the approach from the posterior side with the liquefying by pressing the thermoplastic material against bone tissue and coupling energy into the thermoplastic material, and proposes to use the—intact—cortical bone of the distal side, opposed to the side from which the anchoring takes place, either directly, by the thermoplastic material being pressed against it, or indirectly, by the stabilizing effect of this cortical bone tissue, together with the fact that the cancellous bone in a vicinity of the cortical bone has an enhanced density and an accordingly enhanced strength and stability.

Thus, the present invention is also based on the principle of anchoring by liquefied and re-solidified thermoplastic material but additionally provides an approach for not only anchoring in extended bone tissue such as the vertebral body of a thoracic or lumbar vertebra but in thin, almost plate-like bone tissue in which the opposing (distal) cortical bone serves for forming a broad foot.

More in general, one approach underlying the present invention is to anchor the fastener(s) in a configuration in which the thermoplastic material is pressed into bone tissue of cancellous bone near the cortical bone, not only near the proximal cortical bone ('sub-cortical anchoring') but also near cortical bone tissue that is arranged distally. 'Near' cortical bone tissue (or 'in a vicinity of cortical bone tissue') here implies that the structures into which the thermoplastic material is pressed are within for example not more than 6 mm, especially not more than 4 mm or 3 mm, from the cortical bone in another region than region of the opening in the bone tissue (proximal cortical bone) through which the fastener is placed. Thereby, the thermoplastic material penetrates structures in an immediate vicinity of other cortical bone portions than the proximal cortical bone, resulting in a mechanical support by these (distal or lateral) cortical bone portions.

The invention proposes to provide a fastening structure for each fastener, thus for each fastener there is a place for mechanical coupling to the implant body. This may mean that per fastener a dedicated fastening structure is present. Alternatively, a common fastening structure—such as a slit—may be equipped for cooperating with a plurality of the fasteners.

In embodiments, the implant system includes at least two fasteners or at least three fasteners. Especially, in embodiments with at least three fasteners, the fasteners may be arranged to be not on a common line so that a three-point-anchored system results.

Especially, the implant body may be such that the fasteners are not parallel to each other so that the implant body is secured with respect to all directions, not only by the anchoring effect of the liquefied and re-solidified thermoplastic material but also due to the blocking effect caused by the plurality of non-parallel fasteners that are not all in a common plane.

The energy used for the anchoring process may be mechanical energy, especially mechanical vibration energy. To this end, the fastener may include a proximally facing coupling-in face.

The fastener may be anchored prior to positioning the implant body relative to the tissue. Then, the implantation method includes the additional step of securing the implant body to the fasteners. The fastening structures may then be undercut structures that optionally may be restricted to distal side. This latter option makes possible that the proximal surface is smooth also at the locations of the anchoring structures, so that irritation of soft tissue is minimized.

Alternatively, the fasteners may be anchored after positioning the implant body, for example through through openings in the implant body, which through openings constitute the fastening structures. Such through openings as fastening structures may possibly be broadened towards the proximal side so that a head of the respective fastener may be countersunk.

In a group of embodiments, the fasteners may include an opening extending inwardly, towards proximally, from the distal end. Thus, the fasteners may have a split or cannulated distal end.

The implant system according to embodiments of the invention may be configured to be implanted permanently for stabilization of the spinal column. However, the approach according to the invention is also suitable for temporary stabilization. For example, an implant system according to the invention may be implanted for a demanding surgical operation of the spinal column, so that the surgeon can operate on a stabilized column with the vertebrae in well-defined positions. Especially if the fasteners have a thermoplastic head portion, removal of the system after use is particularly easy, as only such thermoplastic heads have to be removed or disintegrated, for example by drilling.

For example, a recently presented development of a robot for performing spinal surgery by drilling holes for pedicle screws includes a robotic arm that is secured to a vertebrae via a lamina plate, which lamina plate may be an implant body according to the present invention. Another robotic arm of this robot then moves freely and drills the holes for the pedicle screw accurately, taking into account possible movements of the patient during surgery, which movements are automatically followed by the one robotic arm coupled to the lamina plate.

A kit of parts including the implant system may further include a (for example, also custom made) template for drilling the initial openings in the bone tissue and/or a drill for drilling the initial openings.

Mechanical vibration or oscillation suitable for devices according to embodiments of the invention and according methods that include liquefaction of a polymer by friction heat created through the mechanical vibration has preferably a frequency between 2 and 200 kHz (even more preferably between 10 and 100 kHz, or between 20 and 40 kHz) and a vibration energy of 0.2 to 20 W per square millimeter of active surface. The vibrating element (sonotrode) is, e.g., designed such that its contact face oscillates predominantly in the direction of the element axis (longitudinal vibration) and with an amplitude of between 1 and 100 µm, preferably around 10 to 30 µm. Rotational or radial oscillation is possible also.

For specific embodiments of devices, it is possible also to use, instead of mechanical vibration, a rotational movement for creating the named friction heat needed for the liquefaction of the anchoring material. Such rotational movement has preferably a speed in the range of 10,000 to 100,000 rpm. A further way for producing the thermal energy for the desired liquefaction includes coupling electromagnetic radiation into one of the device parts to be implanted and designing one of the device parts to be capable of absorbing the electromagnetic radiation, wherein such absorption preferably takes place within the anchoring material to be liquefied or in the immediate vicinity thereof. Preferably electromagnetic radiation in the visible or infrared frequency range is used, wherein the preferred radiation source is a corresponding laser. Electric heating of one of the device parts may also be possible.

In this text the expression "thermoplastic material being liquefiable e.g. by mechanical vibration" or in short "liquefiable thermoplastic material" or "liquefiable material" is used for describing a material including at least one thermoplastic component, which material becomes liquid (flowable) when heated, in particular when heated through friction, i.e., when arranged at one of a pair of surfaces (contact faces) being in contact with each other and vibrationally or rotationally moved relative to each other, wherein the frequency of the vibration is between 2 kHz and 200 kHz, preferably 20 to 40 kHz and the amplitude between 1 µm and 100 µm, preferably around 10 to 30 µm. Such vibrations are e.g. produced by ultrasonic devices as e.g. known for dental applications.

In this text, generally a "non-liquefiable" material is a material that does not liquefy at temperatures reached during the process, thus especially at temperatures at which the thermoplastic material of the fastener is liquefied. This does not exclude the possibility that the non-liquefiable material would be capable of liquefying at temperatures that are not reached during the process, generally far (for example, by at least 80° C.) above a liquefaction temperature of the thermoplastic material or thermoplastic materials liquefied during the process. The liquefaction temperature is the melting temperature for crystalline polymers. For amorphous thermoplastics the liquefaction temperature is a temperature above the glass transition temperature at which the becomes sufficiently flowable, sometimes referred to as the 'flow temperature' (sometimes defined as the lowest temperature at which extrusion is possible), for example the temperature at which the viscosity drops to below $10^4$ Pa*s (in embodiments, especially with polymers substantially without fiber reinforcement, to below $10^3$ Pa*s)), of the thermoplastic material.

For example, a non-liquefiable material may be a metal, or ceramic, or a hard plastic, for example a reinforced or not reinforced thermosetting polymer or a reinforced or not reinforced thermoplastic with liquefaction temperature considerably higher than the liquefaction temperature of the liquefiable material, for example with a melting temperature and/or glass transition temperature higher by at least 50° C. or 80° C. or 100° C.

For being able to constitute a load-bearing connection to the tissue, the material has an elasticity coefficient of more than 0.5 GPa, preferably more than 1 GPa. The elasticity coefficient of at least 0.5 GPa also ensures that the liquefiable material is capable of transmitting the ultrasonic oscillation with such little damping that inner liquefaction and thus destabilization of the liquefiable element does not occur, i.e. liquefaction occurs only where the liquefiable material is at the liquefaction interface to the stop face. The plastification temperature is preferably of up to 200° C., between 200° C. and 300° C. or even more than 300° C. Depending on the application, the liquefiable thermoplastic material may or may not be resorbable.

Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suited thermoplastic material include any one of the polylactide products LR708 (amorphous Poly-L-DL lactide 70/30), L209 or L210S by Böhringer Ingelheim.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate® by DSM, especially Bionate 75D and Bionate 65D; according information is available on datasheets publicly accessible for example via www-.matweb.com by Automation Creations, Inc.). An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff. (POM—Polyacetal, tradenames Delrin, Tenac, has also been used in endoprostheses by Protec).

The liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

If the liquefiable material is to be liquefied not with the aid of vibrational energy but with the aid of electromagnetic radiation, it may locally contain compounds (particulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% cristallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 µm (contents, preferentially 10-25% by volume), submicron (nanofillers as from precipitation, preferentially plate like aspect ratio>10, 10-50 nm, contents 0.5 to 5% by volume).

A specific example of a material with which experiments were performed was PLDLA 70/30 including 30% (weight percent) biphase Ca phosphate that showed a particularly advantageous liquefaction behaviour.

The material of the implant body may be any material being suitable for surgical applications and being sufficiently stiff. For example, the implant body may be of any material that does not melt at the melting temperatures of the liquefiable material. Especially, it may be of a metal, for example a titanium alloy. A preferred material is titanium grade5. Alternative materials for the implant body are other metals like other titanium alloys, stainless steel, or hard plastics such as PEEK etc.

BRIEF DESCRIPTION OF THE DRAWINGS

In the following, ways to carry out the invention and embodiments are described referring to drawings. The drawings mostly are schematical. In the drawings, same reference numerals refer to same or analogous elements. The drawings show.

DESCRIPTION OF THE PREFERRED EMBODIMENTS

Figure 1A:
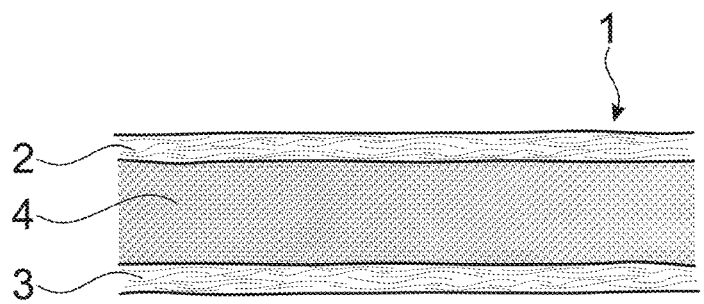
FIGS. 1a-1d bone tissue and an implant system during different stages of an implantation method.

FIG. 1a shows a section through bone tissue of a strong but thin and comparably flat bone, for example a lamina, a vertebral process, a rib or an occiput. The bone includes cortical bone tissue 2, 3 and cancellous bone tissue 4. In this text, the cortical bone portion that is on the side from which the surgeon accesses the bone tissue (the upper side in most figures) is called "proximal cortical bone" and the bone portion on the opposite side is called "distal cortical bone". In a sectional view, the proximal cortical bone tissue is separated from the distal cortical bone tissue, with the cancellous bone tissue in-between. However, in most situations, of course, the proximal and cortical bones are just portions of one cortical bone tissue that runs around the surface of the whole bone.

Figure 1B:
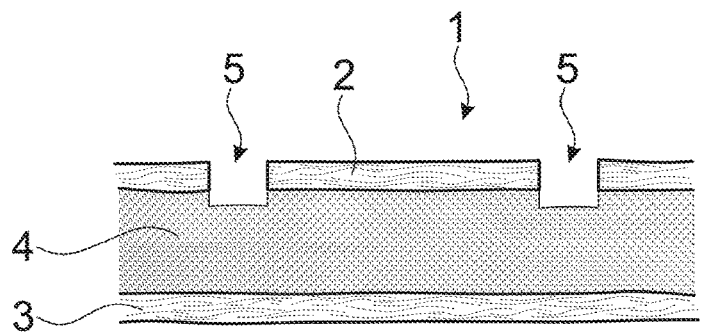

For the implantation process, in a first step the proximal cortical bone tissue is locally removed to yield access openings 5 as shown in FIG. 1b. This may be done by any, for example conventional, surgical means. In an alternative to conventional means, it may be done assisted by ultrasound.

Thereafter, the fasteners are anchored with respect to the bone tissue. In accordance with a first possibility, this may be done after the implant body 20 has been placed. In embodiments of this first possibility, the already the removal of cortical bone tissue may be done with the implant body 20 positioned relative to the bone tissue. The implant body may then serve as a kind of template.

In accordance with a second possibility, the implant body may be poisoned after anchoring.

Figure 1C:
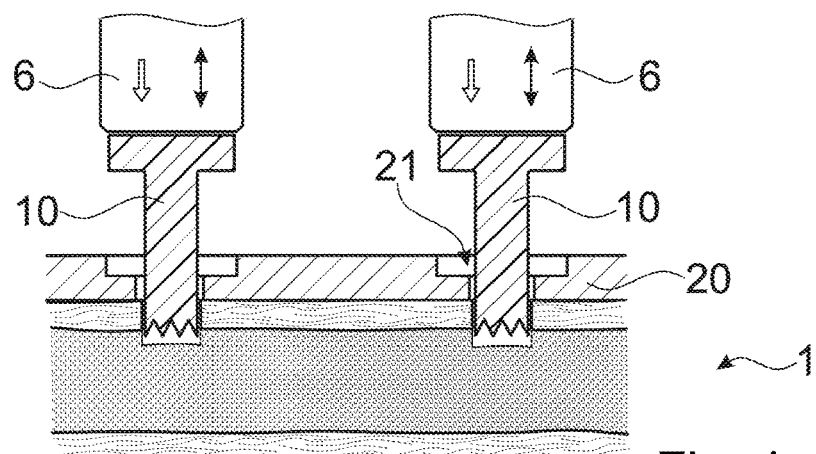
Figure 2:
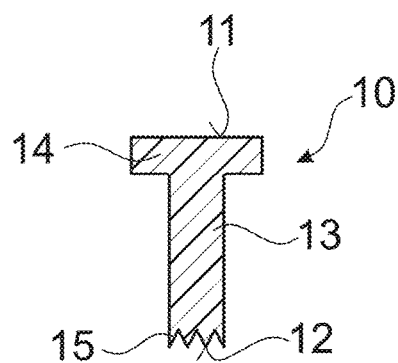
FIG. 2 a fastener.

FIG. 1c illustrates an embodiment in accordance with the first possibility. The implant body 20 is a plate adapted to the proximal surface of the bone. It includes a plurality of attachment structures 21 that are through openings in the depicted embodiment. The fasteners 10, one of which is also illustrated in FIG. 2, extend between a proximal end 11 and a distal end 12. The proximal end 11 constitutes a proximal end face that serves as incoupling face, and the distal end 12 includes optional energy directors 15 that serve for supporting the onset of liquefaction in the subsequent anchoring process. The distal-most portions of the energy directors constitute the end face.

The fasteners are essentially pin-shaped and in the embodiment of FIG. 2 include a shaft portion 13 and a head portion 14.

For the anchoring process, for example a sonotrode 6 is used for sequentially anchoring one fastener 10 after the other (there is also the possibility that a plurality of fasteners is anchored simultaneously by one or more sonotrodes; this option of anchoring a plurality of fasteners simultaneously may especially also be an option if other energy sources than a sonotrode are used, for example radiation or resistive or inductive heating). To this end, the sonotrode 6 presses the fastener 10 into the opening 5 while mechanical vibration energy is coupled into it through the incoupling face until due to friction between the bone tissue and the thermoplastic material and/or due to internal friction the thermoplastic material is sufficiently heated for a flow portion thereof to become flowable. Due to the pressing force, the thermoplastic material is displaced. In this, the distal cortical bone 3 serves as an abutment and as a stop.

Figure 1D:
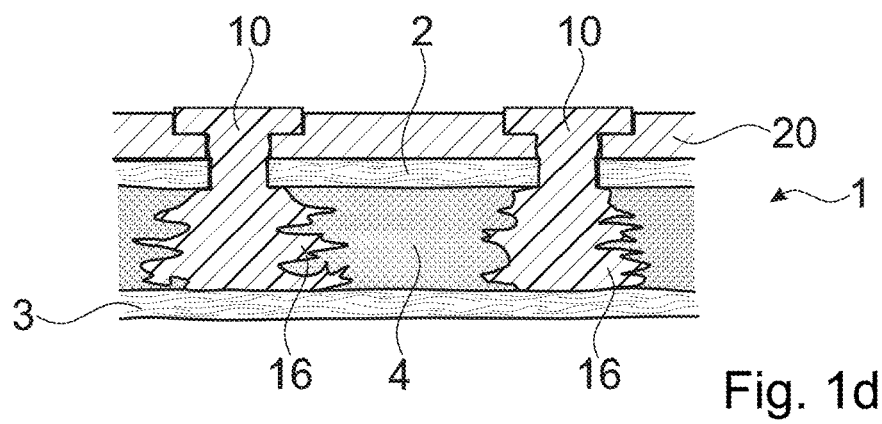

The length of the shaft portion 13 (or of a thermoplastic part thereof) is sufficient for a substantial amount of the thermoplastic material becoming liquefied and being displaced sideways (a forward movement being blocked by the dense tissue of the distal cortical bone 3), resulting in an anchoring foot that, after re-solidification, not only anchors the fastener with respect to the cancellous bone 4 by interpenetrating structures thereof, but may also serve for anchoring the fastener with respect to the proximal cortical bone in a rivet-like manner. FIG. 1d depicts the configuration that results, with the flow portions 16 of the fasteners each forming a foot.

Figure 3:
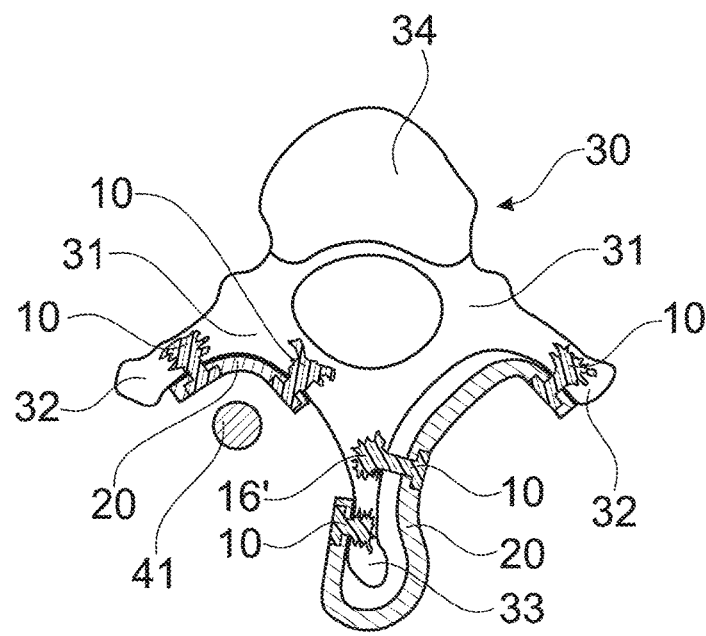
FIGS. 3-5 parts of the skeleton with an implant system.

FIG. 3 shows possible arrangements/applications. A thoracic or lumbar vertebra 30 having a vertebral body 34 is shown, with the lamina 31, the transverse processes 32 and the spinous process 33 being potential anchoring locations.

The implant body 20 shown on the left-hand side is fastened to the lamina 31 and possibly to the transverse process or its onset, whereas the implant body 20 on the left side illustrates the possibilities of also using the spinous process 33 and of shaping the implant body so that it partially encompasses the spinous process (in FIG. 3 the body 20 is illustrated to run posteriorly—or posteriorly-cranially—of the spinous process, but also other geometries would be possible, including portions cranially or caudally of the respective process; between portions of neighboring vertebrae). These possibilities are independent of each other.

In each case, and for any one of the depicted locations of the fasteners, only the proximal cortical bone portion is removed for the anchoring of the respective fastener 10, whereas the opposing (distal) cortical bone is left intact.

The implant body 20 may be a plate plates that itself stabilizes bone tissue portions with respect to each other, for example by fixing different vertebrae to each other (such as for vertebral fusion). In addition or as an alternative, it may serve as anchor for stabilizing implants (like rods, bandages/ribbons, hooks). The left-hand side of FIG. 3 shows, for illustration, an according rod 41 running along a portion of the spine.

The arrangement of the fasteners of the implant system shown on the right side in FIG. 3 is an example of three-point fixation with at least three fasteners that are not in a common plane and that are not parallel to each other (but are skew relative to one another), whereby possible loads on the connection between the bone tissue and the implant body do not only bear on the anchoring of the fasteners but also cause shear forces.

Note that the cross section through the vertebra in FIG. 3 is not a mere horizontal cross section but is simplifying to illustrate all elements of the vertebra relevant in the present context; in fact the different elements are not all in a same horizontal plane. The offset configuration of the pins—which comes about automatically if the implant body follows the anatomy—adds to the stability, and by it not only the stability against pullout towards dorsal but the stability of the entire system may be enhanced due to the skew position and the support by the lamina. The stability of the system may, if required, be further enhanced by the fasteners being hybrids of the thermoplastic material with a potentially more ductile and/or harder other material, such as titanium, steel or a hard plastic like PEEK (see for example FIGS. 6, 7, 19 hereinafter).

Also, the middle one of the three fasteners shown for the implant system of the right side in FIG. 3 is an example of a fastener that does not necessarily have to be pressed against the distal cortical bone tissue as in FIG. 1d but that is inserted into the cancellous bone tissue only, e.g. as demonstrated into the cancellous bone volume of the root of the dorsal processus. The flow portion 16' of the thermoplastic material of this fastener nevertheless due to the location in the root of the dorsal processus is in a vicinity of cortical bone tissue, namely of different cortical bone tissue portions that surround the dorsal processus. Thereby, the fastener is supported at least indirectly also by cortical bone tissue other than the cortical bone through which it penetrates into the cancellous bone underneath.

Figure 4:
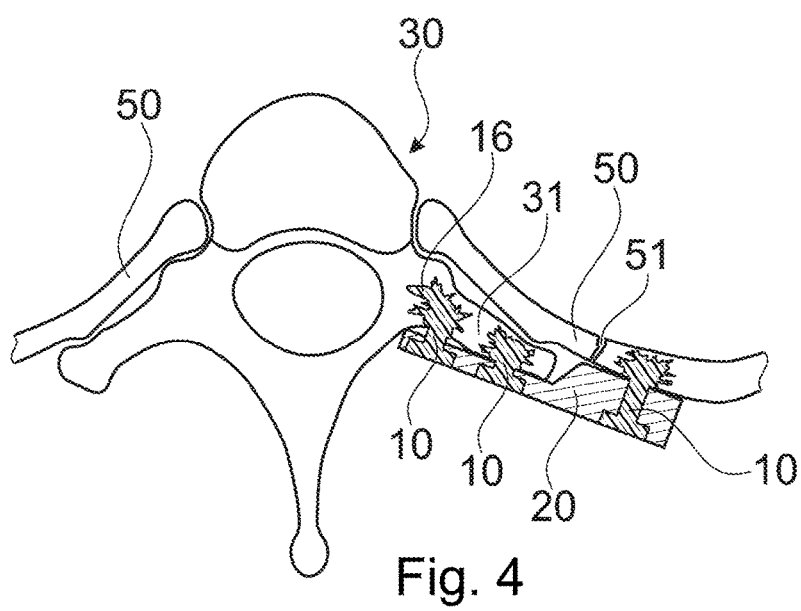

FIG. 4 shows the possibility of fixing another bone to the spinal column, for example a rib 50 having a fracture 51. It would also be possible to anchor a plurality of or all fasteners in bone tissue of the rib—for example on both sides of a fracture—close to the spinal column. Like the above-mentioned fastener of FIG. 3, the fastener shown on the left produces a flow portion 16' that is not necessarily generated in direct physical contact with the cortical bone but that gets into a vicinity of cortical bone tissue, for example the distal cortical bone and possibly other cortical bone near the root of the transverse processus and is thereby supported by cortical bone other than the cortical tissue through which the opening 5 (see FIG. 1b) is made.

Figure 5:
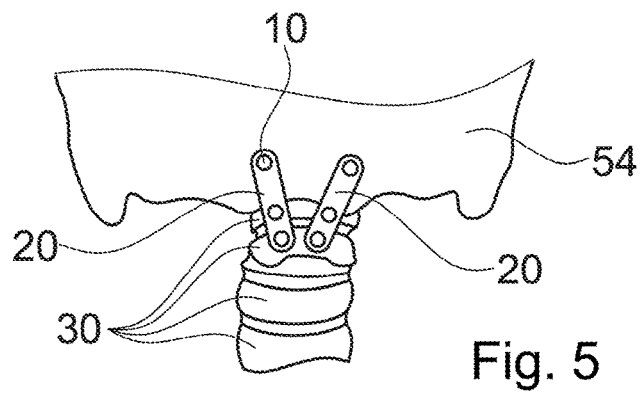

FIG. 5 very schematically shows attaching, by means of the fasteners 10, the implant body 20 to the occiput 54 in addition to a vertebra 30, for example the Axis vertebra and/or the Atlas vertebra.

Figure 6A:
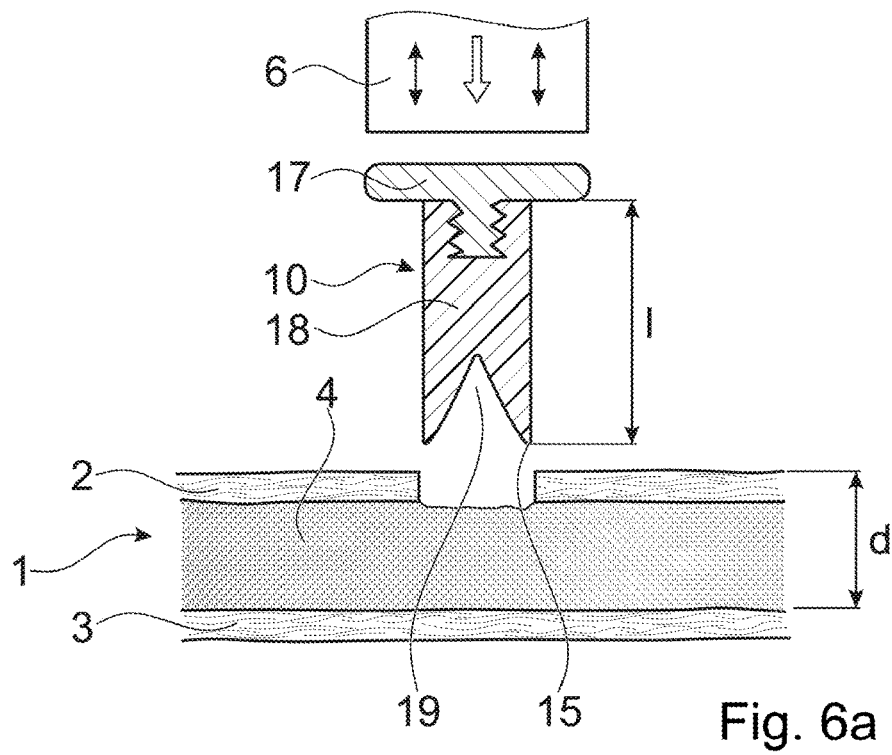
FIGS. 6a-6b an alternative implant system during different stages.
Figure 6B:
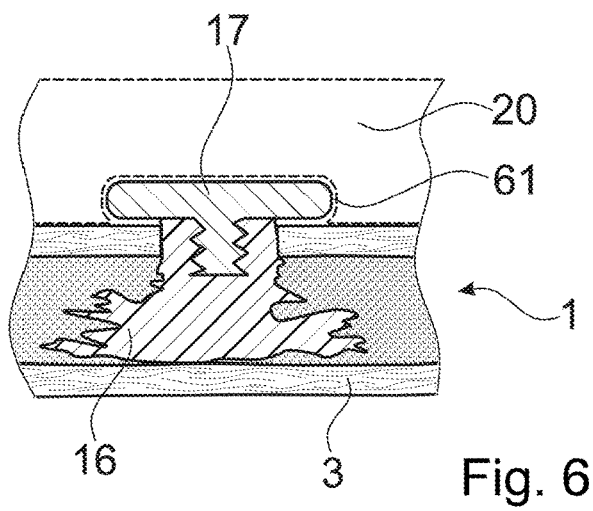

With respect to FIGS. 6a and 6b, showing a fastener at the beginning of the anchoring process and after the anchoring process, respectively, further optional features are discussed, which features are independent of each other and can be realized individually or in any combination:

In contrast to the previously described embodiments, the fastener does not consist of the thermoplastic material but includes a first portion 17 of a non-liquefiable material and a second portion 18 of the thermoplastic material. The second portion 18 forms the distal end (it is not excluded though, that a retractable part of the first portion 17 does also reach to the distal end), for example a retractable outer sleeve portion. In the depicted embodiment, the first part 17 forms a head for serving as a head securing the implant to the bone like in the embodiment of FIG. 1d (with or without the optional counterbore) or for a snap-on connection to the implant body, or similar. Also, in the depicted embodiment the first portion includes structures, for example circumferential grooves and ridges, mechanically anchoring the first portion in the thermoplastic material of the second portion.

The fastener 10 includes an opening 19 extending from the distal end face. In FIG. 6a, the opening is a slit. Such opening may both, assist the initiation of the liquefaction process and/or promote a sideways/lateral movement/flow of thermoplastic material Also, in FIG. 6b, a dashed line illustrates the possibility that the implant body 20 is attached by a snap-on-connection to the fastener (undercut opening 61).

Figure 7:
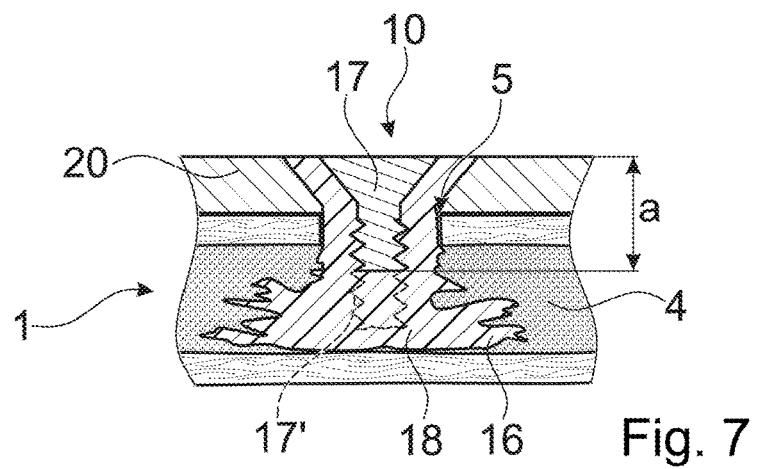
FIG. 7 a further implant system after implantation.

FIG. 7 shows a variant with a first and second portion 17, 18, in which variant the following optional features, which are again independent of each other, are realized:

The attachment structure of the implant body is a countersunk through hole.

The fastener as a whole and/or the first portion thereof are also countersunk.

The second portion 18 forms a collar around the first portion 17 preventing any direct contact between the first portion 17 and the implant body 20.

An axial extension a of the first portion is larger than an axial extension of the attachment location (see also FIGS. 9a and 10) plus the thickness of the proximal cortical bone plus any possible gap between the implant body 20 and the proximal cortical bone, whereby the first portion reaches through the opening 5 into the cancellous bone 4, but does not reach the distal cortical bone. Thereby the first portion 17, which may have a much higher mechanical strength and/or Young's modulus than the second portion 18, may assist in absorbing any possible shear forces on the connection between the implant body and the bone. The dashed line shows the possibility that a shaft portion 17' of the first portion may reach even more deeply into the cancellous bone. but still does not reach the distal cortical bone.

Figure 8:
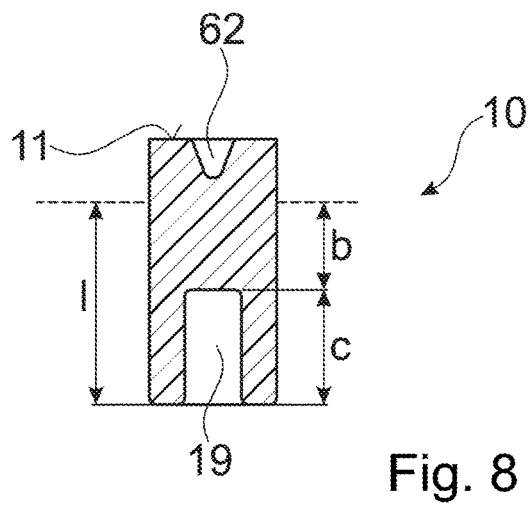
FIG. 8 a fastener.

FIG. 8 shows an even further fastener, in which variant the following optional features, which are again independent of each other, are realized:

The implant includes an opening 19 extending from the distal end, wherein the opening is a central bore extending proximally by a bore depth c from the distal end.

In FIG. 8, the dashed line illustrates the bone level. After anchoring, portions below the dashed line are inside the bone. l denotes the length of the portion of the fastener below the bone level. l will be greater than a cumulated thickness of the proximal cortical bone and the cancellous bone. Thereby, it is ensured that the distal end during the process at least gets close to the distal cortical bone.

In embodiments, the quantity b=l–c may be equal to or greater than the cumulated thickness of the proximal cortical bone and the cancellous bone. Thereby, it is ensured that the thermoplastic material along the full depth of the opening 19 is liquefied and displaced into the bone tissue, whereby no opening remains after the anchoring process (like for example shown in FIG. 7).

The proximal end face is provided with a guiding indentation 62 for a corresponding guiding protrusion of the sonotrode (or other tool) to engage.

Figure 9A:
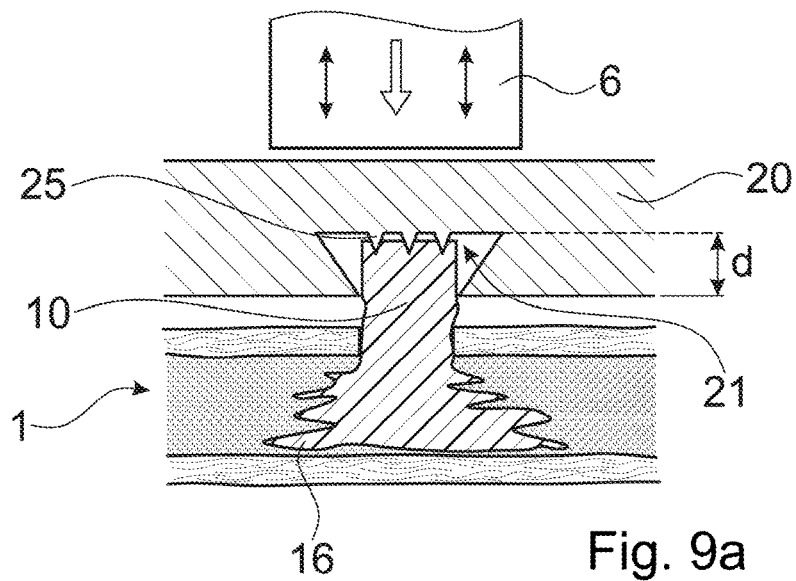
FIGS. 9a-9b yet another implant system during different stages of implantation.
Figure 9B:
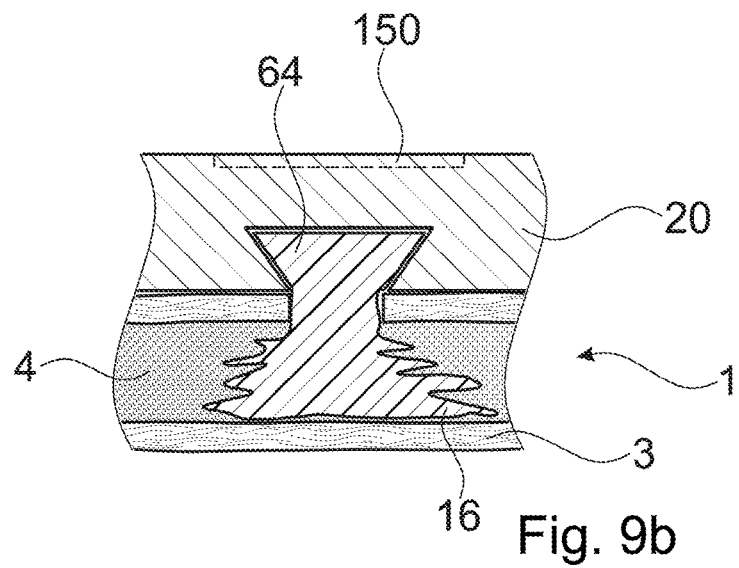

FIGS. 9a and 9b show an implant body 20 with alternative fastening structures and an according alternative way of fastening the fasteners to the fastening structures. The fastening structures 21 are restricted to the distal side (i.e. do not reach through the implant body 20 to the proximal side) and are undercut with respect to proximodistal directions. Optionally, the fastening structures may also be provided with energy directors 25. For fastening, after the anchoring of the fastener 10, the implant body 20 is positioned relative to the anchored fastener with the proximal portion of the fastener reaching into the fastening structure. Then, again energy is coupled into the assembly, for example via the implant body 20, so that thermoplastic material of a proximal portion of the fastener is liquefied and at least partially fills the undercut fastening structure (or other positive-fit structure, for example defined porosity created in an additive manufacturing process of the implant) so as to secure the implant body 20 to the fastener after subsequent re-solidification.

In embodiments in which the fastening structure does not reach to the proximal side, the depth d of the fastening structure may be smaller than a thickness of the implant body. This also holds true for fastening structures restricted to the distal side other than the structure of FIG. 9a, for example a snap-in indentation, or an indentation into which a corresponding portion of the fastener is hammered to be secured in a Morse taper fashion, etc.

Especially in embodiments in which the fastening structures are restricted to the distal side, the implant body 20 may include marks or a guiding structure for the sonotrode. FIG. 9b shows an optional positioning indentation 150 into which the sonotrode 6 may engage. As an alternative to this, a guiding structure may include a comparably smaller guiding hole in the proximal end face of the implant body, which guiding hole is configured to accommodate a guiding protrusion of the sonotrode.

Figure 10:
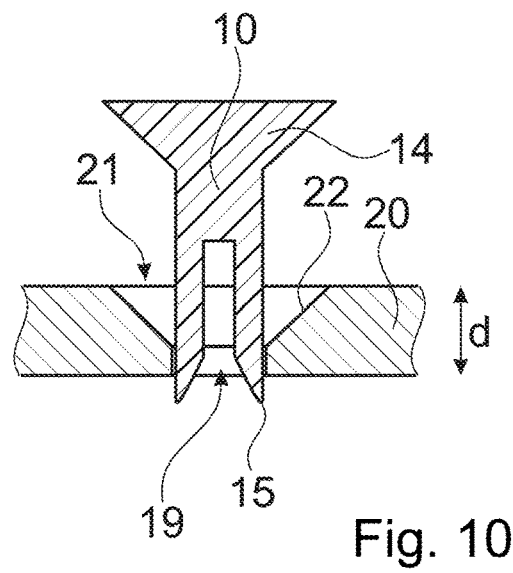
FIG. 10 a further implant system.

The variant of FIG. 10 combines the following features that are independent of each other:

The fastening structure 21 is countersunk (defining a tapered abutment face 22 for a corresponding distally facing surface portion defined by the head 14).

The fastener has an accordingly shaped head portion 14;

The fastener 10 consist of the liquefiable material

The fastener 10 has an opening 19 being a slit.

The depth d of the fastening structure corresponds to the thickness of the implant body at the location of the fastening structure.

Figure 11:
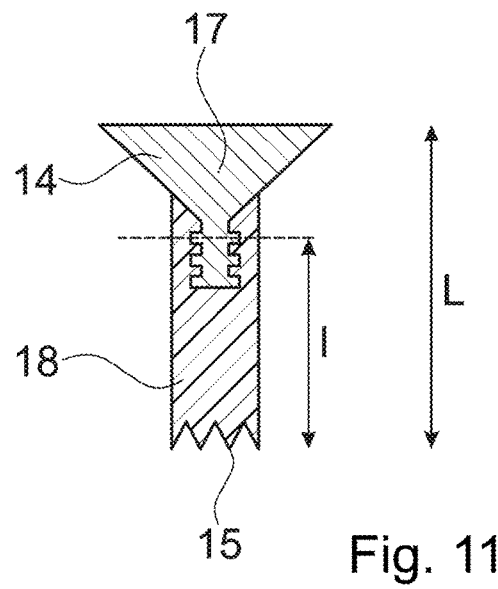
FIG. 11 an alternative fastener.

FIG. 11 shows a variant of the fastener of FIG. 10 with a tapering head 14, which variant however includes a first non-liquefiable portion 17 and a second, liquefiable portion 18 that in FIG. 11 does not have any opening. l again denotes the length of the portion of the fastener below the bone level.

The following pertains as option to all embodiments:

In many embodiments, the length l of the portion below the bone level is sufficient for the the distal cortical bone 3 serves as an abutment and as a stop during the anchoring process in which the fastener is pressed towards distally. This yields the above-mentioned design criterion:

$$l > t_2 + t_4,$$

where $t_2$ is the thickness of the proximal cortical bone, $t_4$ is the thickness of the cancellous bone hence and $t_2+t_4$ is the cumulated thickness In embodiments, l may be greater than 1.5 times or even 2 times this cumulated thickness $t_2+t_4$.

For the overall length L of the fastener, the design criterion becomes:

$$L > t_2 + t_4 + d + g + p,$$

where d is the depth of the fastening structure, g is the width of a potential gap between the bone and the implant body (in many applications, g is 0 or almost 0, i.e. the implant body lies against the bone), and p is the axial extension of a possible portion of the fastener protruding above the proximal face of the implant body. In many applications, including the embodiments of FIGS. 3-11, p is 0.

Figure 12:
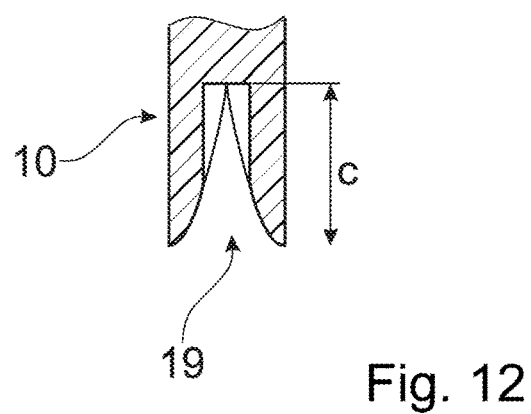
FIG. 12 the distal end of a fastener.

For the depth c of a possible opening 19 measured from the distal end of the fastener (FIG. 12), an according possible design criterion is:

$$c \leq L - t_2 - t_4 - d - g - p$$

Thus the depth c of a possible opening 19 according to this optional design criterion is not larger than the difference between the initial length L and the length after the anchoring process, wherein the final length is assumed to be $t_2+t_4+d+g+p$ (which is correct if the distal end after the process coincides with the proximal surface of the distal cortical bone.

In reality, of course, the separation between the cortical bone and the cancellous bone may be gradual, the surfaces between the cortical bones and the cancellous bones for example being defined by median surfaces of a transition zone.

Figure 13:
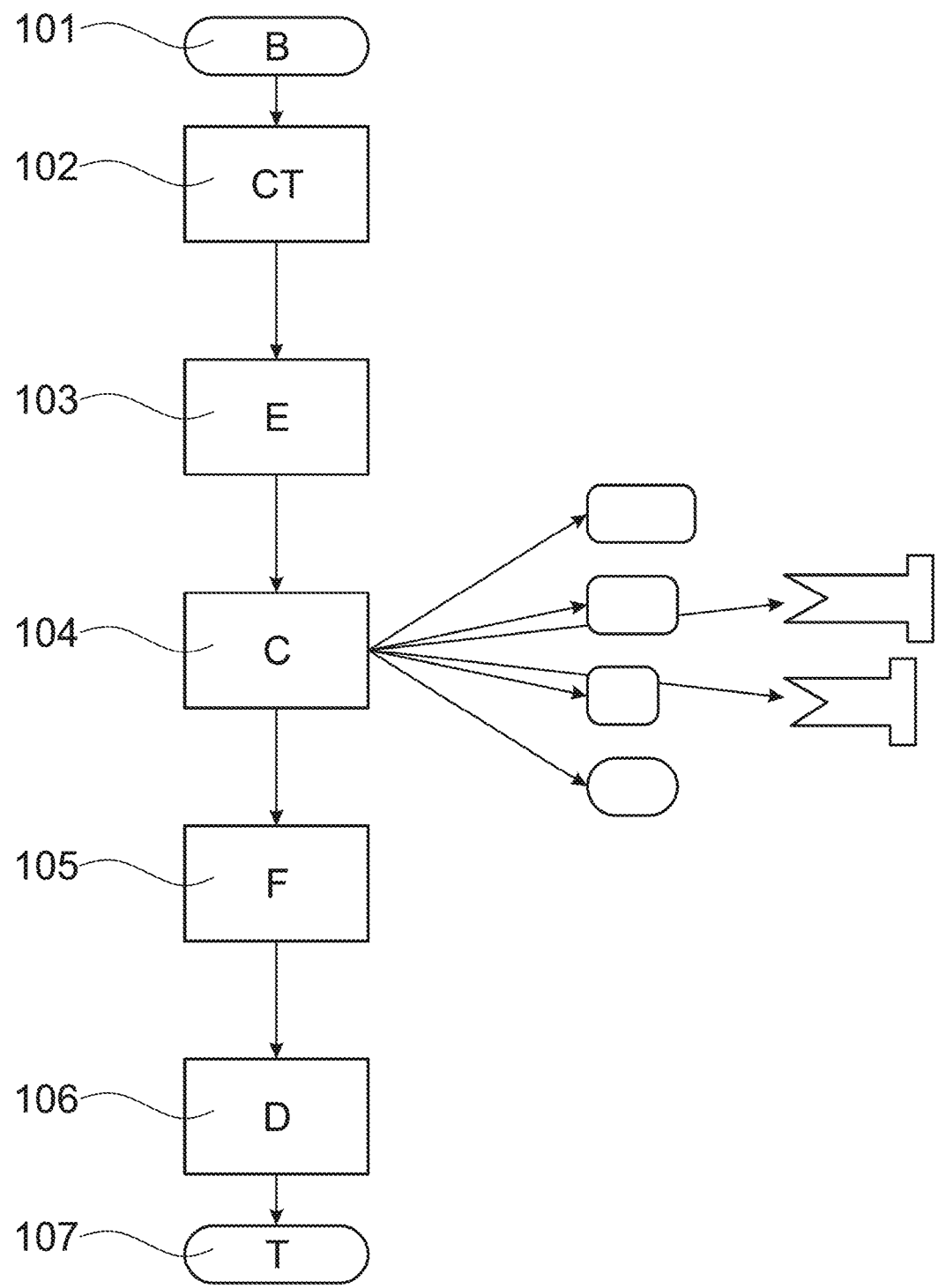
FIGS. 13 and 14 flowcharts of methods of obtaining an implant system.

FIG. 13 shows a possible sequence of steps of a method for manufacturing an implant system according to the present invention. After start 101, data, especially 3D-image data of the relevant part of the patient's spine and/or other bone is obtained, for example by computer tomography 102. Then, a competent implant designer or a surgeon or possibly computer program evaluates the patient's needs (step 103) and chooses a fitting implant body and fitting fasteners from a pre-defined collection of possible implant body designs and possibly also from a pre-defined collection of possible fastener designs (step 104). For example, the fasteners are chosen to meet the above design criteria in view of the properties of the bone in which they are to be anchored. The evaluation step 103 and/or the choosing step 104 may be carried out in a computer aided manner, for example using a 3D-model of the relevant tissue portions of the patient. The evaluation and choosing steps 103, 104 may optionally be combined, for example if the competent person tries different implant system models and chooses the one considered best.

In embodiments, the pre-defined implant body designs include different implant body shapes and sizes, but the exact position of the fastening structures is not yet defined. Then, in a further step 105, that may be combined with the evaluation step 103 and/or the choosing step 104 the position of the fastening structures is determined. In practice, it may be important that the positions of the locations on the bone where the fasteners are anchored and also other parameters like anchoring depth, angle, etc. are well adjusted to the quality and geometry of the tissue, especially in situations where the bone tissue is weakened or damaged.

In embodiments with not pre-defined fastening structures, in a further step 106 the fastening structures are physically manufactured. This may be done by drilling or another ablative process from a pre-manufactured implant body, or alternatively the implant body including the fastening structures may be custom manufactured.

After termination 107, the surgical operation may be carried out as described hereinbefore.

Figure 14:
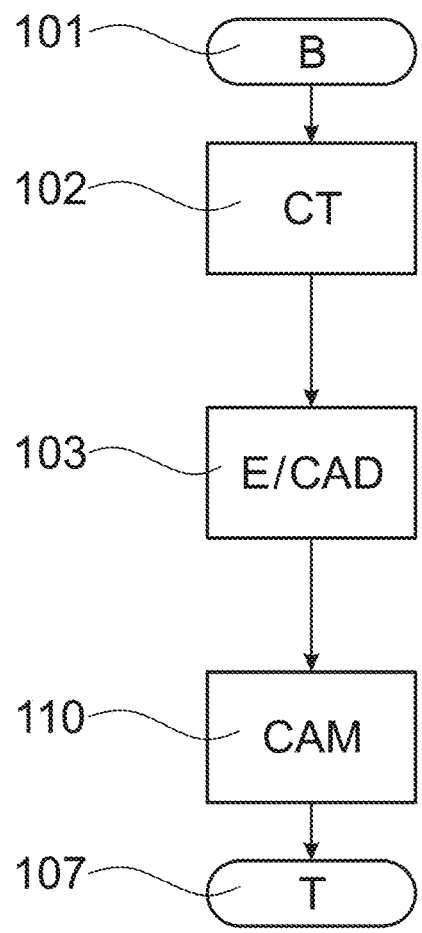

In a variant of the process, not only the fastening structures but the entire implant body is custom-manufactured. In this alternative process (FIG. 14) the evaluation step 103 includes a sub-step of designing the implant body based on patient data obtained in the data acquisition step 102. This includes positioning and designing the fastening structures. Subsequently, the implant body is custom manufactured (step 110) from computer data by any suitable computer aided manufacturing (CAM) method, for example by a 3D-printing method.

The method of obtaining a suitable implant system may be varied in many ways:

For example for standard cases, instead of obtaining 3D-image patient data and using these data for choosing/designing the implant body and the fasteners, also other information can be used for choosing the implant body and the fasteners. For example, the competent person may consult well-known information that allows him to estimate the relevant sizes based on his knowledge and/or a table, etc. Such information may especially depend on known quantities like the body size, weight, sex, age, etc.

Instead of manufacturing the fastening structures in a manufacturing step 106, the implant body may have pre-determined locations (such as along a slit, at positions with a porosity to which the fastener may be coupled, etc.). Then, the fastening structure determination step is translated into according information or a template or similar for the surgeon.

Generally, in embodiments, the implant system in addition to the implant body and the fasteners also includes a drilling jig that defines the position and angle of the drilling holes in the bone tissue, as well as, for example by means of a tube across which the drill is guided across the jig, the depth of the hole. Especially, such drilling jig may make sure that the drill never pierces the distal cortical bone but this distal cortical bone remains intact and that the drill will drill across the proximal cortical bone to yield access to the cancellous bone.

In embodiments in which the system has a drilling jig, the method of obtaining the implant system will further include the step of obtaining the drilling jig. For this (independent of whether the implant body is custom manufactured or not), the following options exist:

Choosing from a plurality of pre-defined and possibly pre-manufactured drilling jigs;

Using a pre-defined and possibly pre-manufactured drilling jig body and adjusting at least one parameter, for example a position, angle and/or depth of the drilling hole(s).

Custom manufacturing the drilling jig.

Figure 15A:
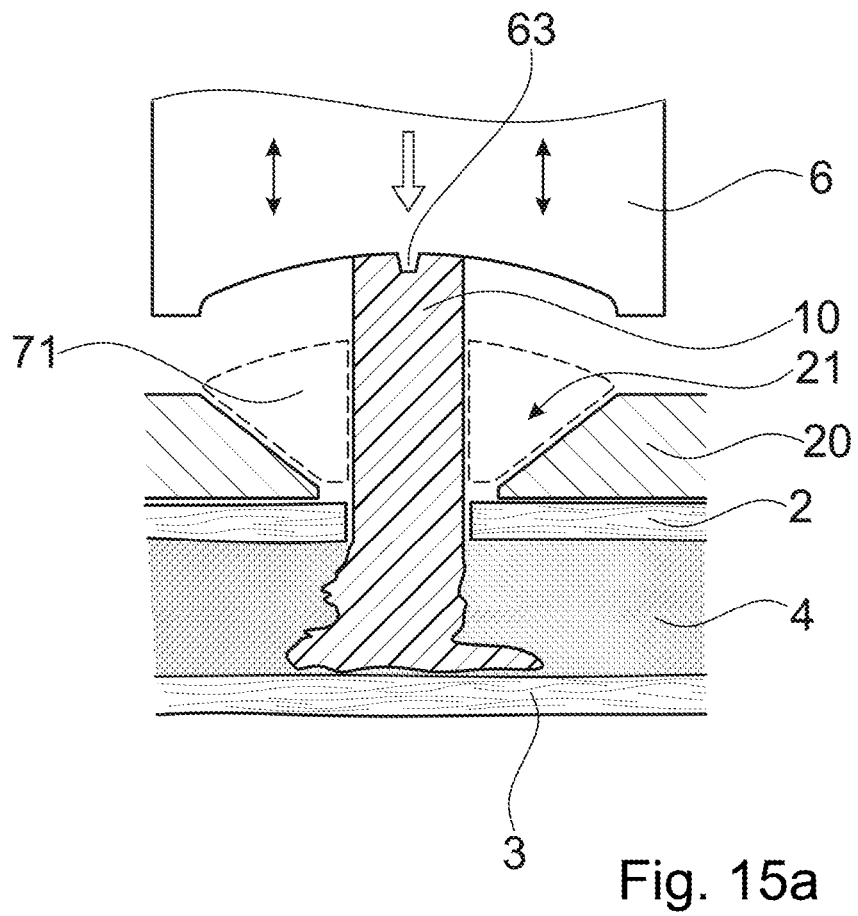
FIGS. 15a and 15b a further implant system during different stages of implantation.
Figure 15B:
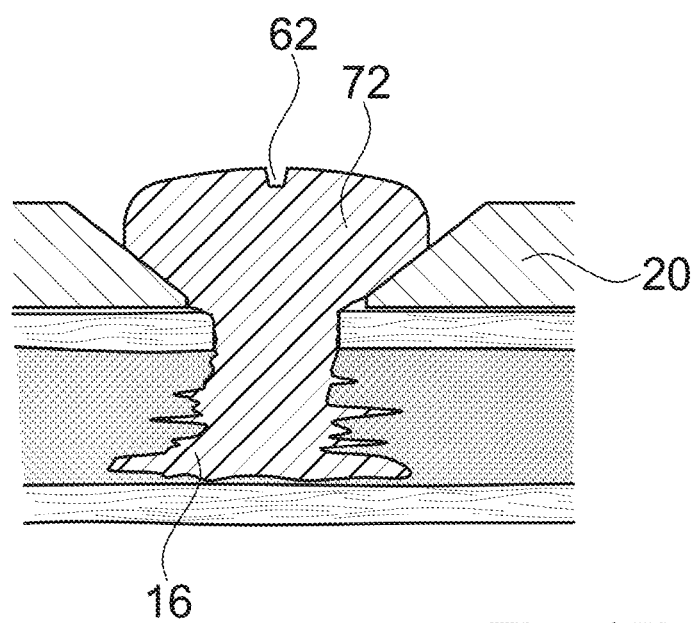

FIGS. 15a and 15b illustrate a possibility of forming a proximal part of the fastener in situ. Thereby, a possible issue may be addressed: Depending on the situation and bone quality, a required length of the fastener shaft may be not precisely known. An excess length of the fastener may be used for forming a head portion, especially by impinging energy that makes proximal portions of the fastener flowable and by correspondingly shaped shaping portions of the sonotrode and/or the implant body. The shaping portions of the sonotrode 6 and the implant body 20 together define a volume 71 (dashed line in FIG. 15a) for a proximal flow portion. Depending on the excess length, the volume 71 in the process may be completely filled or only partially filled. FIG. 15b illustrates the situation after the process (with a guiding indentation 62 that during the process cooperates with a guiding protrusion 63 of the sonotrode 6). The volume 71 is partially filled by material that after re-solidification forms the proximal head 72.

Instead of an empty volume 71 or in addition thereto, the implant body 20 could also define a porous region that may be interpenetrated by thermoplastic material of the fastener. Also this will yield an effect of securing the implant body 20 to the tissue via the fastener.

For the head forming, two options (that may be combined with each other) exist:

According to a first option, the properties of the tissue will after some time cause a substantial rise in resistance against a further movement of thermoplastic material into the tissue, for example because available cavities are filled and/or because outermost parts of the flow portion in the tissue have started to re-solidify because they are too far from the spot where heat is generated by the friction. Due to this rise in resistance, more energy absorption will take place proximally, which effect may ultimately be used for the head forming.

According to a second option, a two-step process is carried out. In a first step, the (distal) flow portion is caused to flow. Then, the energy input is interrupted or reduced to allow the flow portion to re-solidify at least partially. When again energy is coupled into the system, the mechanical resistance will be higher than initially, and this will lead to the effect of proximal heat generation, used for the head forming.

In the previous embodiments, the attachment structure 21 was assumed to be constituted by a circular through opening, possibly countersunk. However, the approach according to the present invention is also suited for not rotationally symmetrical shapes of the attachment structure and or of fastener cross sections because the process of anchoring the fasteners with respect to bone tissue does not necessarily involve rotating the fasteners.

Figure 16:
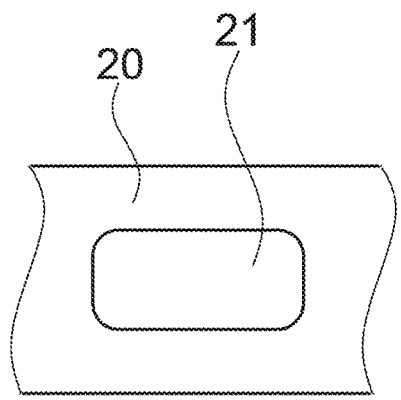
FIGS. 16-18 alternative attachment structures.

FIG. 16 very schematically illustrates this possibility, with an attachment structure 21 being constituted by an oblong, possibly countersunk through opening. Generally, for any embodiment any attachment structure and approximately or precisely adapted fastener cross section is possible. Not rotationally symmetrical structures feature the advantage of providing additional stability.

Figure 17:
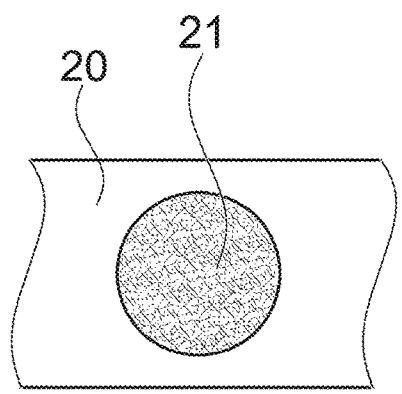

FIG. 17 shows an even further possibility. Namely, the attachment structure 21 is constituted by an open porous region of the implant body 20. The fastener, which in this embodiment may consist of the thermoplastic material, is pressed through the open porous region into the bone tissue while the energy impinges. In this embodiment, a full cross section of the fastener is liquefied by being pressed through the open porous region, and it is not possible to exert a mechanical pressure from the fastener onto the bone tissue during the anchoring. This embodiment is therefore especially suited for situations where the proximal cortical bone has locally been removed (c.f. FIG. 1*b*) and the cancellous bone underneath offers comparably little resistance against a flow of thermoplastic material penetrating into its structures, also the liquefaction temperature of the thermoplastic material in such embodiments should not be too high.

Figure 18:
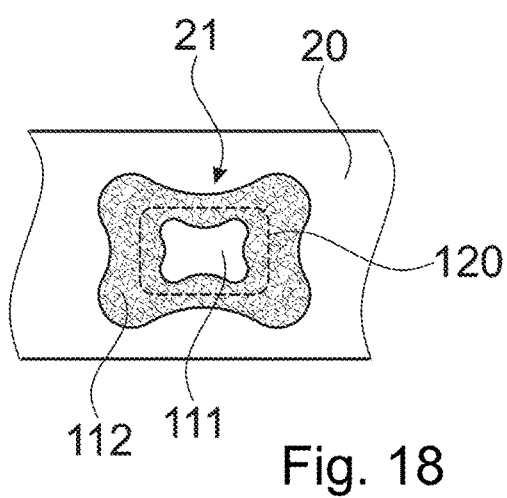

FIG. 18 shows a variant in which the fastening location 21 is constituted by a through opening 111 and, in a vicinity thereof, an open porous structure 112. The fastener in this may have a cross section slightly larger than the cross section of the through opening 111 (as illustrated by the dashed line 120) and/or may be guided such that during anchoring it comes into contact also with the open porous structure, whereby a portion of the thermoplastic material is liquefied in contact with the open porous structure 112 and penetrates into it. This provides an additional relative fixation of the implant body to the bone tissue, as for example taught in WO 2008/034 276.

Such open porous structure may after the anchoring process also become interpenetrated by bone tissue for long-term stability, as for example taught in WO 2017/001851.

The concepts taught in FIGS. 16-18 are options for any embodiment of the present invention, including the embodiments taught hereinbefore.

Figure 19:
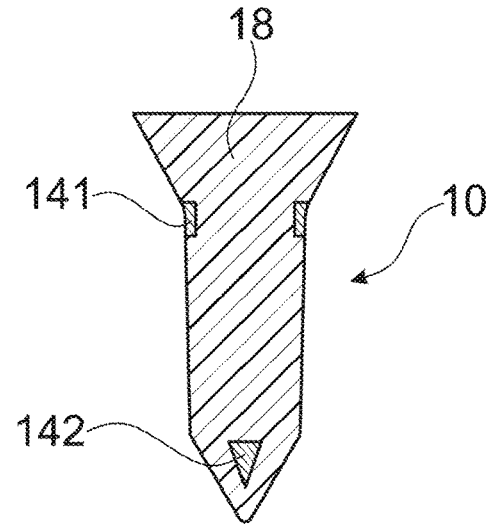
FIG. 19 an even further fastener.

FIG. 19 yet depicts a variant of a fastener 10 that essentially consists of the thermoplastic material but that in addition to the thermoplastic portion includes a first, proximal marker 141—being ring-shaped and surrounding a proximal region of the shaft—and a second, distal marker 142 close to the distal end. It would also be possible to provide a fastener with a single marker. The marker is of a material visible in an X-Ray and may serve for locating the fastener also if no magnetic resonant imaging is made.

In any embodiment, if the implant system has to be removed, it may be sufficient to remove or disintegrate, for example using a drill, the fastener head. If necessary, a marker of the kind shown in FIG. 20 may help for precisely locating, especially for minimally invasive surgery. A guiding indentation 62 of the kind shown in FIG. 15*b* but being an optional feature of the other embodiments, too, may be used as a centering aid for the drill.

Also, it is possible to use a template for the drill, both, for drilling access openings 5 in the bone tissue and/or if necessary later for a removal drill for drilling into the fastener heads. After the fastener heads are removed or set free, the implant body may just be lifted away. The rest of the fasteners may remain integrated in the bone tissue. In embodiments where the fasteners are in any case only needed temporarily (for example because the implant body is used temporarily only or if the fastener body is equipped for osseointegration), the fasteners may be of a resorbable thermoplastic material.

Figure 20:
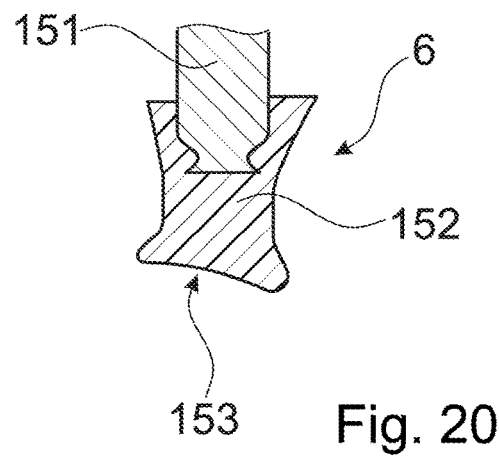
FIG. 20 a sonotrode having a custom made plastic sonotrode head.

FIG. 20 very schematically illustrates the option of a sonotrode having a plastic sonotrode head 152 attached to a sonotrode body 151, the head for example being of PEEK. Providing a head (or an entire sonotrode) of such a material has for example the following advantages:

Noise reduction compared to a fully metallic sonotrode;

The sonotrode/sonotrode head can be custom manufactured by 3D printing, for example to have a tailor-made distal outcoupling surface 153 adapted to the (for example also tailor-made) surface of the implant body and thus ultimately to the patient's anatomy.

A custom manufactured sonotrode head may for example be especially advantageous in situations like the one illustrated in FIGS. 9*a* and 9*b* where the sonotrode impinges on the fastener via the implant body, with or without guiding indentation 150, because she shape of the implant will often not allow for a flat surface but often has a curved surface following the anatomy.

What is claimed is:

1. An implant system, comprising:
    an implant body, the implant body having a shape being adapted to be fastened to a posterior side of the spinal column, and
    a plurality of fasteners, each fastener including a proximal head portion and a shaft portion extending distally from the head portion,
    wherein the implant body is a plate having a shape adapted to a surface of the spinal column and following the patient's anatomy,
    wherein the implant body comprises at least one fastening structure, the at least one fastening structure comprising a through opening and a shallow indentation around the through opening,
    wherein each fastener extends between a proximal end and a distal end and comprises a thermoplastic material in a solid state, the thermoplastic material being liquefiable by energy impinging on the fastener,
    wherein each fastener is equipped for being anchored in the bone tissue of the spinal column in an anchoring process by energy coupled into the fastener to at least partially liquefy the thermoplastic material,
    wherein a flow portion of the thermoplastic material is pressed into bone tissue and, after re-solidification, anchors the fastener in the bone tissue, and
    wherein each fastener is equipped for cooperating with the at least one fastening structure to secure the implant body to the bone tissue by the shaft portion extending through the through opening into the bone tissue and the head portion being in the shallow indentation.

2. The implant system according to claim 1, wherein the thermoplastic material comprises thermoplastic material portions at a distally facing end face of the fastener, and
    wherein the anchoring process comprises the fastener being pressed against bone tissue by a pressing force acting from a proximal side in addition to energy being coupled into the fastener.

3. The implant system according to claim 2, wherein a length of the fasteners is sufficient for the distal end face to reach through an opening in proximal cortical bone of the bone tissue and through cancellous bone of the bone tissue to be pressed against distal cortical bone of the bone tissue.

4. The implant system according to claim 3, wherein for at least one fastener a length/along a proximodistal axis a portion below the bone level is greater than a cumulated thickness of the proximal cortical bone and of the cancellous bone.

5. The implant system according to claim 4, wherein the length/is greater than a cumulated thickness of the proximal cortical bone and of the cancellous bone by at least a factor 1.5.

6. The implant system according to claim 1, wherein the implant body is custom manufactured.

7. The implant system according to claim 1, comprising at least three fasteners that are not in a common plane and are not parallel.

8. The implant system according to claim 1, wherein the at least one fastening structure is not rotationally symmetrical.

9. A method of obtaining an implant system according to claim 1, the method comprising:
- choosing an implantation location relative to a patient's spinal column,
- obtaining information on bone size and shape of the patient,
- choosing an adapted implant body shape and size and an adapted fastener size, and
- taking the implant body of the adapted implant body shape and size and the fasteners of the adapted fastener size.

10. The method according to claim 9, wherein obtaining the information comprises using a 3D-imaging process for obtaining 3D image data on the patient.

11. The method according to claim 9, wherein taking the implant body of the adapted implant body shape and size comprises custom manufacturing the implant body.

12. The method according to claim 11, wherein custom manufacturing comprises using 3D-data to shape the implant body adapted to the patient's skeleton.

13. The method according to claim 11, wherein custom manufacturing comprises choosing a pre-defined implant body shape from a plurality of pre-defined implant body shapes, and adding the at least one fastening structure to the implant body.

14. The method according to claim 9, wherein choosing an adapted fastener size comprises configuring the fastener so that the thermoplastic material when being pressed into bone tissue reaches a region in a vicinity of cortical bone tissue different from cortical bone tissue around an opening through which the fastener extends into the bone tissue.

* * * * *